(12) United States Patent
Vonk et al.

(10) Patent No.: US 8,761,881 B2
(45) Date of Patent: Jun. 24, 2014

(54) INTRACARDIAC POLARIZATION SIGNAL STABILIZATION

(75) Inventors: Bernardus F. M. Vonk, Wehl (NL); Gustaaf A. P. Stoop, Dieren (NL); Volkert Zeijlemaker, Landgraaf (NL)

(73) Assignee: Medtronic, Inc., Minneapolis, MN (US)

( * ) Notice: Subject to any disclaimer, the term of this patent is extended or adjusted under 35 U.S.C. 154(b) by 1119 days.

(21) Appl. No.: 11/459,469

(22) Filed: Jul. 24, 2006

(65) Prior Publication Data

US 2008/0243203 A1 Oct. 2, 2008

Related U.S. Application Data

(63) Continuation of application No. 10/422,894, filed on Apr. 24, 2003, now Pat. No. 7,363,078.

(51) Int. Cl.
*A61N 1/37* (2006.01)
(52) U.S. Cl.
USPC .......................................................... 607/27
(58) Field of Classification Search
USPC ............................................... 607/9, 27, 13
See application file for complete search history.

(56) References Cited

U.S. PATENT DOCUMENTS

| | | | |
|---|---|---|---|
| 4,305,396 A | 12/1981 | Wittkampf et al. | |
| 4,527,568 A | 7/1985 | Rickards | |
| 4,644,954 A | 2/1987 | Wittkampf et al. | |
| 4,972,834 A | 11/1990 | Begemann et al. | |
| 5,172,690 A * | 12/1992 | Nappholz et al. | 607/13 |
| 5,184,615 A * | 2/1993 | Nappholz et al. | 607/14 |
| 6,067,472 A * | 5/2000 | Vonk et al. | 607/28 |

\* cited by examiner

*Primary Examiner* — Eric D. Bertram
(74) *Attorney, Agent, or Firm* — Reed A. Duthler

(57) ABSTRACT

Polarization signals, which represent voltages measured at a pacemaker electrode, are not constant and may drift. Polarization signal drift, which often precedes undesirable pace polarization artifacts, is more significant when the pacemaker is inhibited from providing an electrical stimulation to the patient's heart. The present invention provides an implantable system and methods for stabilization of a polarization signal. Electrical pulses may be applied to stabilize a polarization signal. In one implementation of the invention, polarization signal stabilization may be used as part of process to terminate tachycardia.

10 Claims, 9 Drawing Sheets

INTRACARDIAC POLARIZATION SIGNAL STABILIZATION

CROSS-REFERENCE TO RELATED APPLICATIONS

This application is a continuation of U.S. application Ser. No. 10/422,894 filed Apr. 24, 2003 entitled "Intracardiac Polarization Signal Stabilization", now U.S. Pat. No. 7,363,078.

FIELD OF THE INVENTION

This invention relates generally to the field of implantable medical devices, and more particularly to implantable heart monitors and therapy delivery devices.

BACKGROUND OF THE INVENTION

A wide variety of implantable heart monitors and therapy delivery devices have been developed including pacemakers, cardioverter/defibrillators, heart pumps, cardiomyostimulators, ischemia treatment devices, and drug delivery devices. Most of these cardiac systems include electrodes for sensing and sense amplifiers for recording and/or deriving sense event signals. Often the sense event signals are utilized to control the delivery of the therapy in accordance with a predefined algorithm.

Implantable pulse generators are well known in the prior art. Most demand pacemakers include sense amplifier circuitry for detecting intrinsic cardiac electrical activity so that the devices may be inhibited from generating unnecessary output electrical stimulating pulses when a heart is functioning properly. Dual-chamber cardiac pacemakers typically have separate sense amplifiers for atrial and ventricular sensing. The sense amplifiers detect the presence of intrinsic signals, such as P-waves occurring naturally in the atrium and R-waves occurring naturally in the ventricle. Upon detecting an intrinsic signal, sense amplifier circuitry generates a digital signal for output to other components which inhibit the delivery of a pacing pulse to the corresponding chamber.

It is desirable to accurately and reliably measure the response of the heart to an electrical stimulating pulse. Measuring such a response permits the determination of a patient's stimulation threshold, or the minimum energy a stimulating pulse must contain for a cardiac response to be evoked. Once a patient's stimulation threshold is determined, the energy content of stimulating pulses may be adjusted to avoid delivering pulses having unnecessarily high energy content. Minimizing the energy content of stimulating pulses is believed to have physiological benefits, and additionally reduces power consumption, a key concern in the context of battery-powered implantable devices.

Detection and measurement of the response of the heart to an electrical stimulating pulse may also be useful in controlling a pacemaker's pacing rate, for ascertaining the physiological effect of drugs or for diagnosing abnormal cardiac conditions.

Immediately following delivery of a pacing pulse to cardiac tissue, a residual pace polarization artifact (also called a post-pace polarization artifact or a pace polarization signal) is generated by the charge induced in the electrode tissue interface by delivery of a pacing pulse. If the pacing pulse captures the heart and causes an evoked response in the cardiac tissue, then an evoked response signal is superimposed atop the typically much larger amplitude pace polarization artifact. As a result, conventional pacemakers or pacemaker-cardioverter-defibrillators ("PCD's") either cannot differentiate, or have difficulty differentiating, between pace polarization artifacts and evoked response signals. This problem is further complicated and exacerbated by the fact that residual pace polarization artifacts typically have high amplitudes even when evoked response signals do occur. Consequently, it becomes difficult, if not impossible, to detect an evoked response signal using a conventional pacemaker or PCD sense amplifier employing linear frequency filtering techniques. As a result, most pacemakers cannot discern between pace polarization artifacts and evoked response signals.

Most pacemakers employ sensing and timing circuits that do not attempt to detect evoked response signals until the pace polarization artifact is no longer present or has subsided to some minimal amplitude level; only then is sensing considered reliable. In respect of capture detection, where the pacemaker detects whether the pacing pulse to the cardiac tissue evoked an effective stimulated response, such sensing typically occurs a significant period of time after the evoked response signal has already occurred. As a result, most pacemakers cannot detect evoked response signals with any degree of confidence.

The generation and delivery of an electrical pulse gives rise to the storage of charge in the electrode tissue interface. Such charge storage produces pace polarization artifacts, which typically have much larger amplitudes than those corresponding to electrical signals arising from an intrinsic heartbeat or a stimulated response. Pace polarization artifacts may also interfere with the detection and analysis of a stimulated or evoked response to a pacing pulse. Thus, a need exists in the medical arts for determining reliably whether or not an evoked response signal has occurred in a pacing environment.

Pace polarization artifacts typically arise due to the electrode-tissue interface storing energy after a pacing stimulus has been delivered. There are typically two electrode-tissue interfaces in a pacing circuit: one for the tip electrode, and one for the ring (or canister) electrode. The stored energy dissipates after the pace event, creating the after-potential.

In respect of the impedance sensed by a pacemaker's internal circuitry, the total load of the pacing circuit comprises the impedance of the lead itself, the electrode-tissue interface impedances, and the impedance of the body tissue bulk. The impedances of the body tissue and the lead may be modeled as a simple series bulk resistance, leaving the electrode-tissue interfaces as the reactive energy absorbing/discharging elements of the total load. The tip electrode is the primary after-potential storage element in comparison to the case and ring electrodes. In a pacing circuit, a ring electrode typically stores more energy than does a case electrode due to differences in electrode areas.

Several methods have been proposed in the prior art for improving an implantable device's ability to detect and measure evoked responses. For example, U.S. Pat. No. 5,172,690 to Nappholz et al., entitled "Automatic Stimulus Artifact Reduction for Accurate Analysis of the Heart's Stimulated Response," hereby incorporated by reference herein its entirety, proposes a tri-phasic stimulation waveform consisting of precharge, stimulus, and postcharge segments. The duration of the precharge segment is varied until the amplitude of the pace polarization artifact is small compared to the evoked response.

Other disclosures related to the same general subject matter include the U.S. Patents listed below in Table 1.

| Country | Pat. No. | Inventor/Applicant | Issue Date |
| --- | --- | --- | --- |
| U.S.A. | 4,644,954 | Wittkampf et al. | Feb. 24, 1987 |
| U.S.A. | 4,972,834 | Begemann et al. | Nov. 27, 1990 |
| U.S.A. | 5,954,756 | Hemming et al. | Sep. 21, 1999 |

All patents listed in Table 1 above are hereby incorporated by reference herein in their respective entireties. As those of ordinary skill in the art will appreciate readily upon reading the Summary of the Invention, Detailed Description and Claims set forth below, many of the devices and methods disclosed in the patents of Table 1 may be modified advantageously by using the teachings of the present invention.

BRIEF SUMMARY OF THE INVENTION

In general, the invention provides solutions to problems existing in the prior art by providing devices and methods for improved pacemaker operation. For example, the invention provides an implantable medical device system designed to stabilize pacemaker electrode polarization signal drift.

In general, polarization signals, which are the voltages measured at the interface between the pacemaker electrode and the patient's tissue, are not constant. In the absence of frequent applied stimulation, polarization signals vary or drift. In cases where pacing pulses are applied on a frequent basis, the voltage at the electrode-tissue interface remains comparatively constant or stable, with comparatively little drift. When a pacing pulse is applied to an electrode that has experienced little polarization signal drift, compensation techniques may be used effectively to minimize the resulting pace polarization artifact. After long periods of inhibition, i.e., long periods in which no stimulation is applied, the drift is often substantial, and the electrode-tissue interface is unstable. Prior art devices do not address the problem of drift, and do not stabilize the polarization signal at the electrode-tissue interface prior to stimulation following a long period of inhibition.

The amount of drift depends generally upon factors such as the electrode being used, the pulse shape and the characteristics of the patient's body. When a pacing pulse is applied to an electrode that has experienced polarization signal drift, a large pace polarization artifact usually results. Techniques for compensating for pace polarization artifacts are less effective if the polarization signal has drifted. Thus, although a pace polarization artifact may be minimized in a sequence of electrical stimulations, a significant pace polarization artifact may reappear following a stimulation that comes after a lengthy period of inhibition.

The invention provides apparatus and methods for stabilizing the electrode voltage, counteracting the effects of drift. One object and advantage of the invention is to facilitate beat-to-beat capture. Significant drift can lead to high pace polarization artifacts, which interfere with detection of invoked responses and thus hinder capture. By counteracting drift after long periods of inhibition, the invention reduces pace polarization artifacts and enhances capture.

A further object and advantage of the invention is its usefulness in termination of tachycardia, or rapid heart beat. Anti-tachycardia pacing depends upon coordinating stimuli with the cardiac activity, but pace polarization artifacts interfere with the measurement of cardiac activity. Counteracting drift can reduce pace polarization artifacts and can make cardiac monitoring more efficient. With improved cardiac monitoring, anti-tachycardia paces may be applied at appropriate times to break the tachycardia.

A further advantage and object of the invention is that it may be implemented using existing hardware, thus requiring no additional space, no new connections, and no supplemental equipment.

Various embodiments of the invention are set forth in the accompanying drawings and the description below. Other features and advantages of the invention will become apparent from the description, the drawings, and the claims.

DETAILED DESCRIPTION OF THE INVENTION

Figure 1:
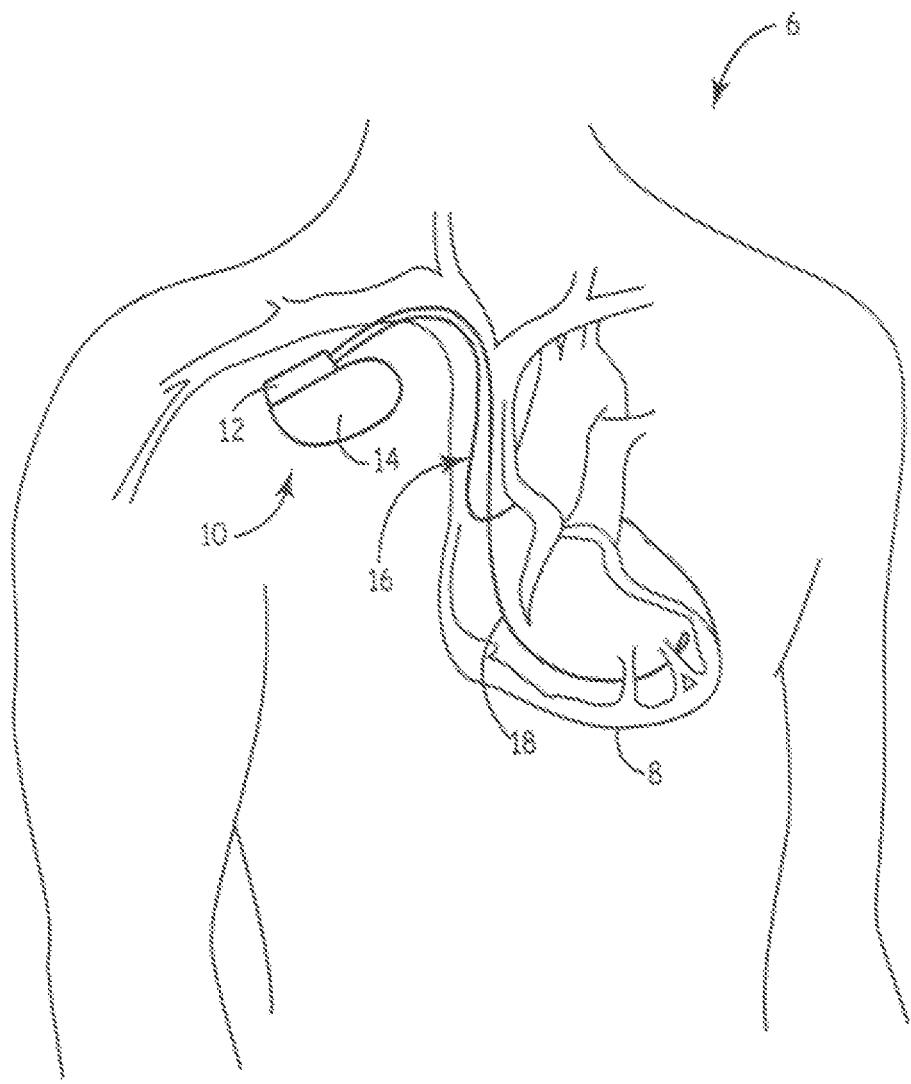
FIG. 1 illustrates an implantable medical device system in accordance with an embodiment of the invention implanted in a human body

FIG. 1 is a simplified schematic view of one embodiment of implantable medical device ("IMD") 10 of the present invention implanted within a human body 6. IMD 10 comprises hermetically sealed enclosure 14 and connector module 12 for coupling IMD 10 to pacing and sensing leads 16 and 18 that are implanted near the proximal side in contact with the heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
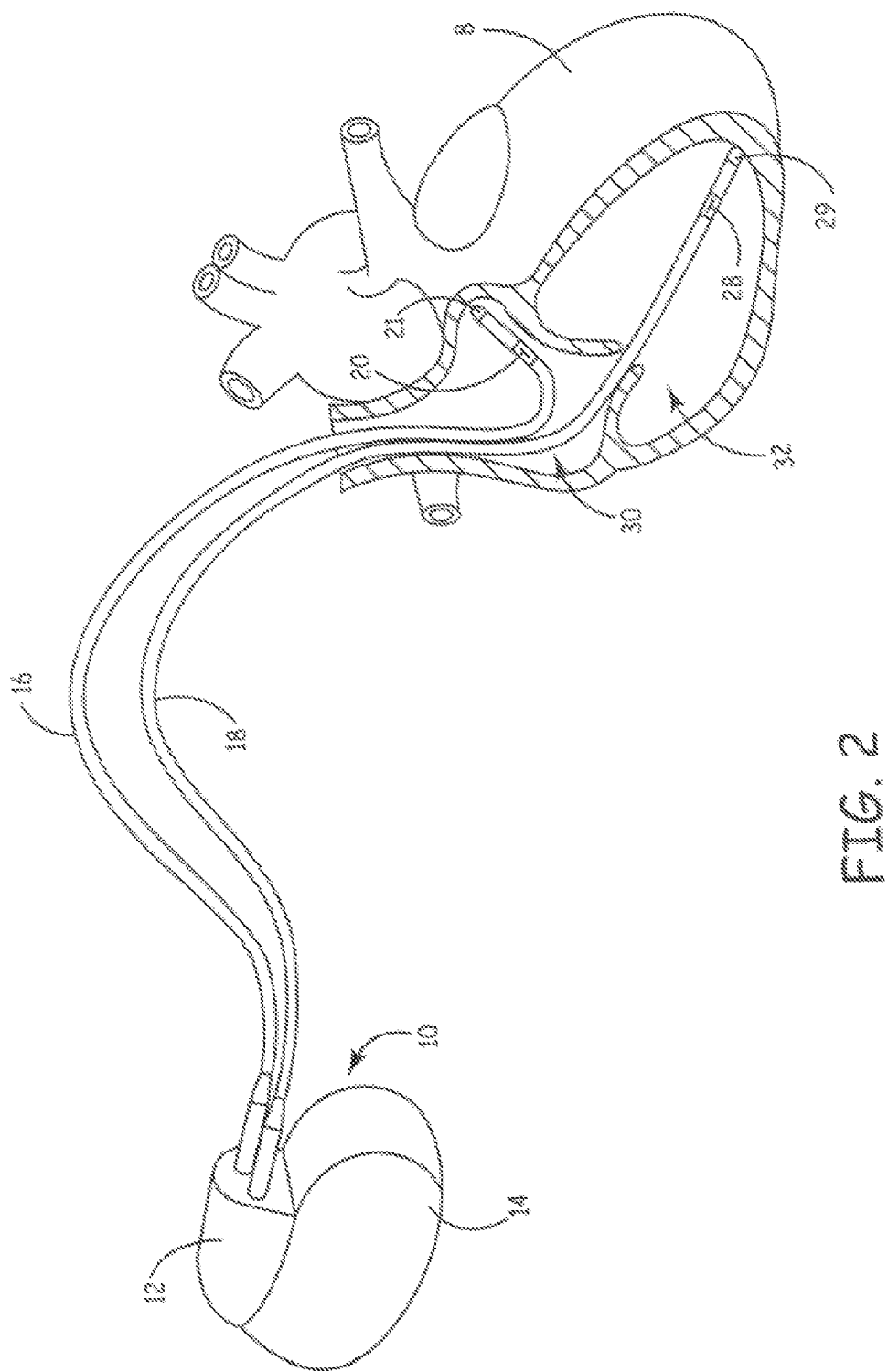
FIG. 2 illustrates one embodiment of an implantable pacemaker device system in accordance with the present invention coupled to a human heart.

FIG. 2 shows connector module 12 and hermetically sealed enclosure 14 of IMD 10 located in and near heart 8. Atrial and ventricular pacing leads 16 and 18 extend from connector module 12 to the right atrium 30 and ventricle 32, respectively, of heart 8. Atrial electrodes 20 and 21 disposed at the distal end of atrial pacing lead 16 are located in the right atrium 30. Ventricular electrodes 28 and 29 at the distal end of ventricular pacing lead 18 are located in the right ventricle 32.

Figure 3:
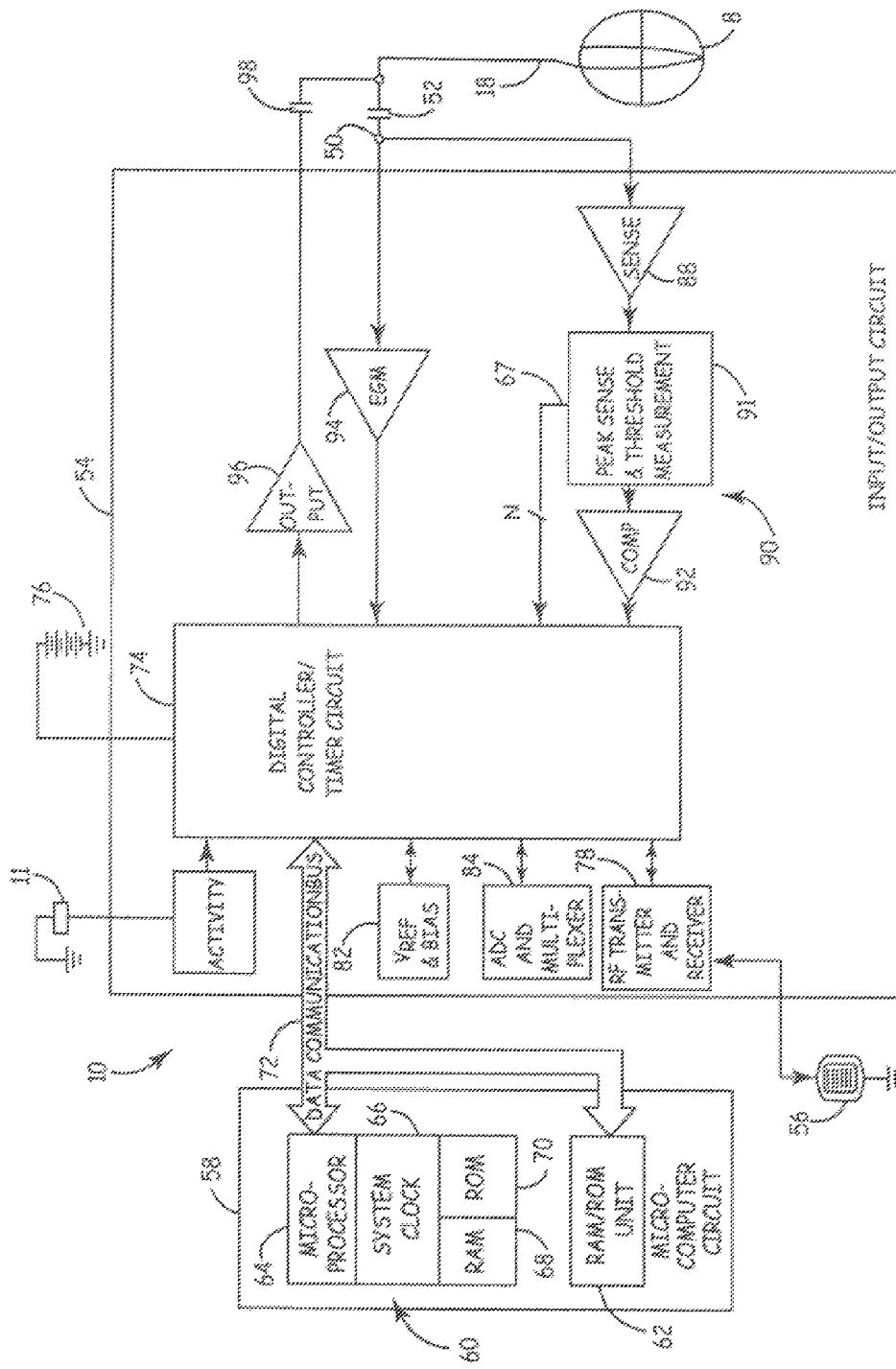
FIG. 3 is a block diagram illustrating the various components of one embodiment of an implantable pacemaker device configured to operate in accordance with the present invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the figures). One such programmer is the commercially available Medtronic Model 9790 programmer, which is microprocessor-based and provides a series of encoded signals to IMD 10, typically through a programming head that transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58, including rate response algorithms.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish an overall escape interval of the IMD 10 as well as various refractory, blanking and other timing windows for controlling the operation of peripheral components disposed within input/output circuit 54.

Digital controller/timer circuit 74 is preferably coupled to sensing circuitry 91, including sense amplifier 88, peak sense and threshold measurement unit 90 and comparator/threshold detector 92. Digital controller/timer circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8. Also, some embodiments of the invention can use active polarization compensation.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
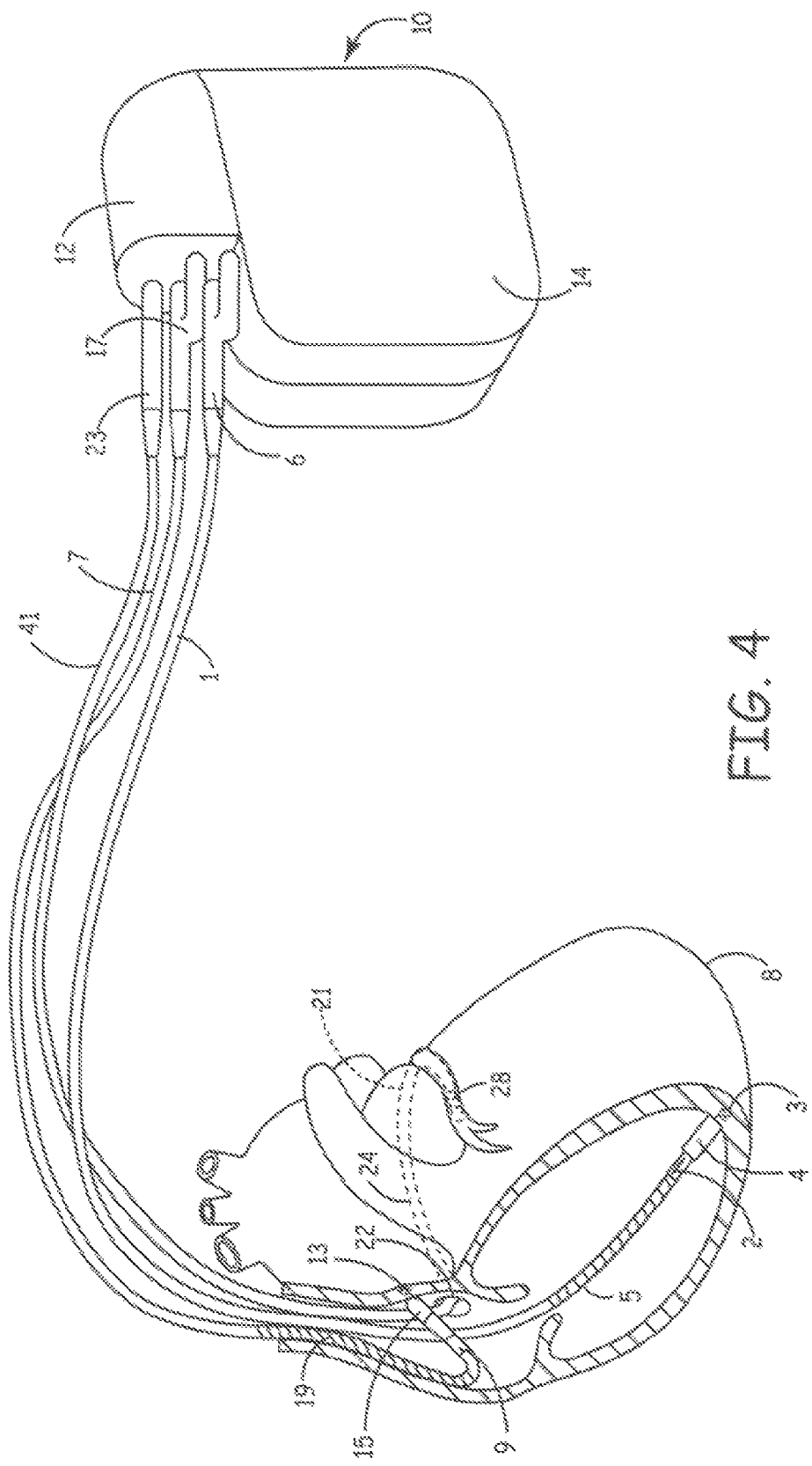
FIG. 4 illustrates one embodiment of an implantable pacemaker cardioverter defibrillator in accordance with the present invention coupled to a human heart.
Figure 5:
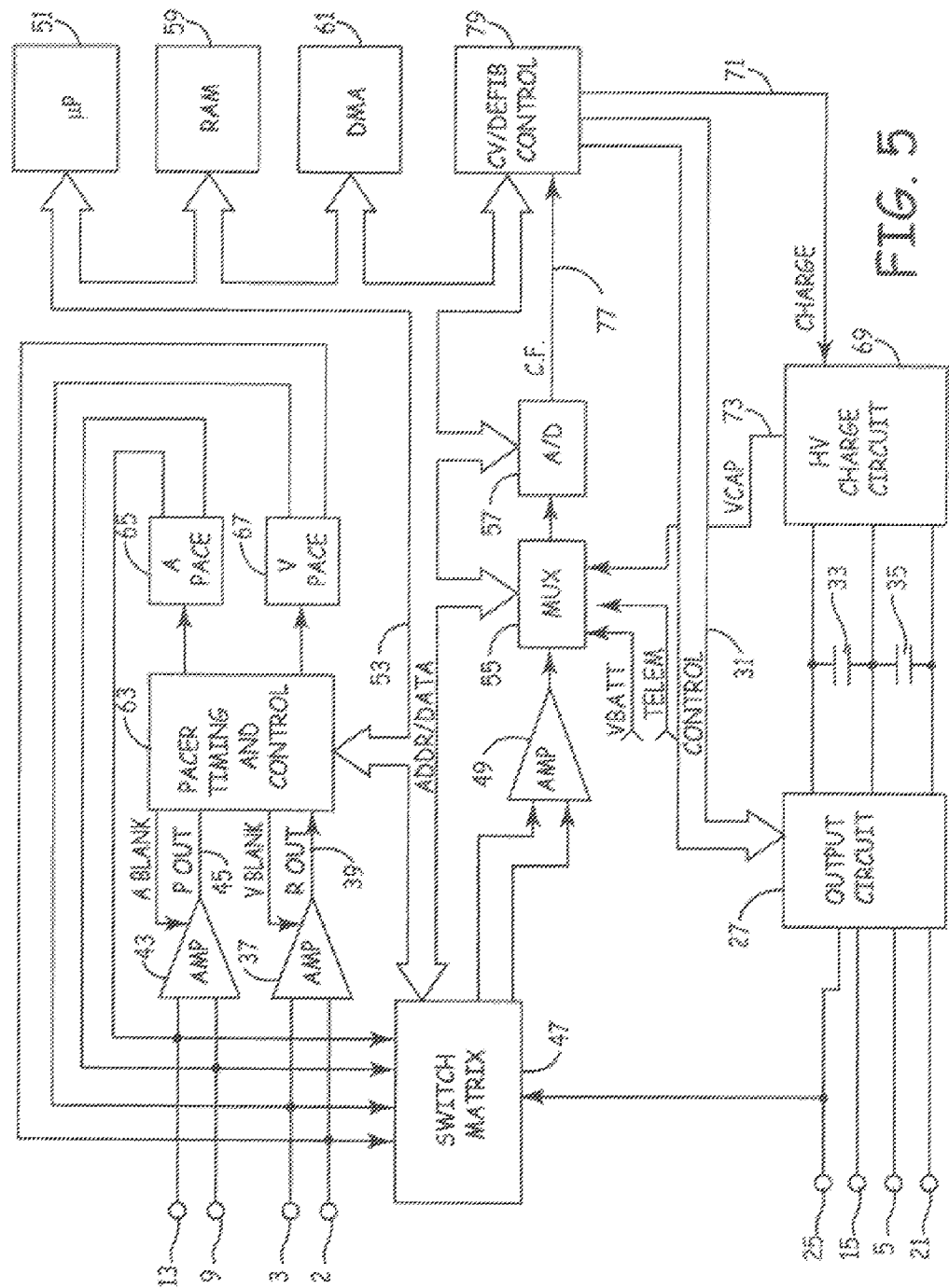
FIG. 5 is a block diagram illustrating the various components of one embodiment of an implantable pacemaker cardioverter defibrillator configured to operate in accordance with the present invention.

FIGS. 4 and 5 illustrate one embodiment of IMD 10 and a corresponding lead set of the present invention, where IMD 10 is a PCD. In FIG. 4, the ventricular lead can take the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead 41 shown in FIG. 4 is located within the coronary sinus and great vein of heart 8. At the proximal end of the lead is connector plug 23 carrying an electrical connector coupled to the coiled conductor. The coronary sinus pacing lead 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 79 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference herein in its entirety.

Switch matrix 47 is used to select which of the available electrodes are coupled to wide band (0.5-200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular (AV) pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt-driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726, 380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7-10, 1986, IEEE Computer Society Press, pages 167-170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541-547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 79, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Delivery of cardioversion or defibrillation pulses is accomplished by output circuit 27 under the control of control circuitry 79 via control bus 31. Output circuit 27 determines whether a monophasic or biphasic pulse is delivered, the polarity of the electrodes and which electrodes are involved in delivery of the pulse. Output circuit 27 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
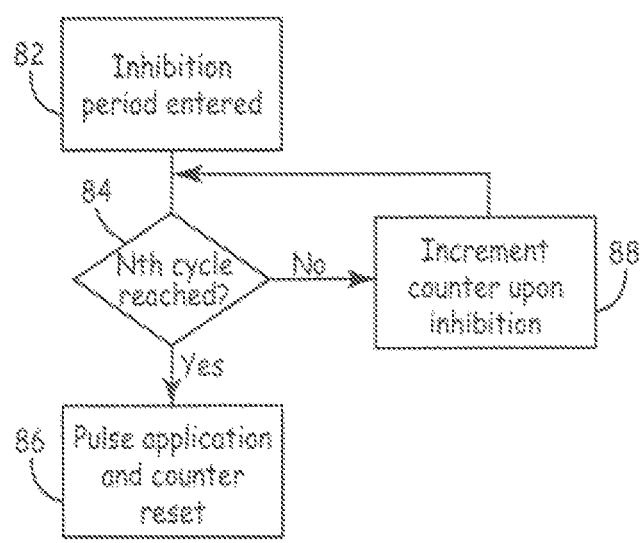
FIG. 6 is a flow chart illustrating one mode of operation of an implantable medical device operating according to the invention.

FIG. 6 is a flow chart illustrating one embodiment of a process in which IMD 10 may be programmably configured to stabilize polarization signal drift. In general, IMD 10 operates to deliver electrical pulses to heart 8 only when such pulses are needed. If no stimulation is required, IMD 10 will enter an inhibition period 82. During inhibition period 82, IMD 10 inhibits the production of stimulating pulses, and polarization signal drift may occur. The more extensive the inhibition period, the more drift is likely, and the larger the resulting pace polarization artifact when stimulation resumes.

Drift may be counteracted by application of one or more electrical pulses that alter the level of charge stored at the electrode-tissue interface. One process for counteracting drift, therefore, is to apply one or more pulses following a predetermined period of inhibition. By altering the level of stored charge, the pulses stabilize the electrode-tissue interface. The pulses may be effective, i.e., timed to evoke a contraction of cardiac tissue, or the pulses may be non-effective, i.e., not timed to evoke a contraction of cardiac tissue.

One embodiment of the invention counts the number of cardiac cycles occurring with inhibition, i.e., without a pacemaker-supplied pacing stimulus, and provides a pulse 86 on the Nth cycle. The number N may vary from patient to patient, and depends upon the electrode being used for pacing, the pulse shape, and the characteristics of the patient's body. For a typical patient, N may be on the order of 10 to 100 cardiac cycles. When a cardiac cycle occurs without a pacemaker-supplied stimulus, an inhibition period 82 is entered. During inhibition period 82, IMD 10 determines 84 whether N inhibitions have occurred, i.e., whether N cardiac cycles have taken place without stimulation. If N inhibitions have not occurred, a counter increments 86 upon each inhibition. If N cycles have occurred, one or more pulses are applied and the counter resets 86. Microcomputer circuit 58 may include algorithms to use past responses as a basis for determining the most beneficial number of pulses for a particular patient with a particular inhibition period.

A pulse 86 may be timed to evoke ventricular depolarization, thus evoking a QRS complex (denoting ventricular depolarization) and a following T-wave (denoting ventricular repolarization). Many IMD's sense the Q-T interval as a part of their rate response and the measured Q-T interval is useful to the rate response algorithm. An advantage of such a pulse is that it can be used to update the Pace-T time, i.e., the measured time between pacing stimulus and T-wave, which in turn is a useful indicator for capture or loss of capture in a beat-to-beat capture verification system.

Alternatively, pulse 86 may be timed to evoke a trigger pace, i.e., timed to coincide with the natural pacing stimulus of the heart. Such pulses result in fusion complexes, where the natural stimulation and the IMD stimulation fuse into a single stimulation signal. Such stimulation does not disturb the intrinsic timing of the natural cardiac cycle.

Figure 7:
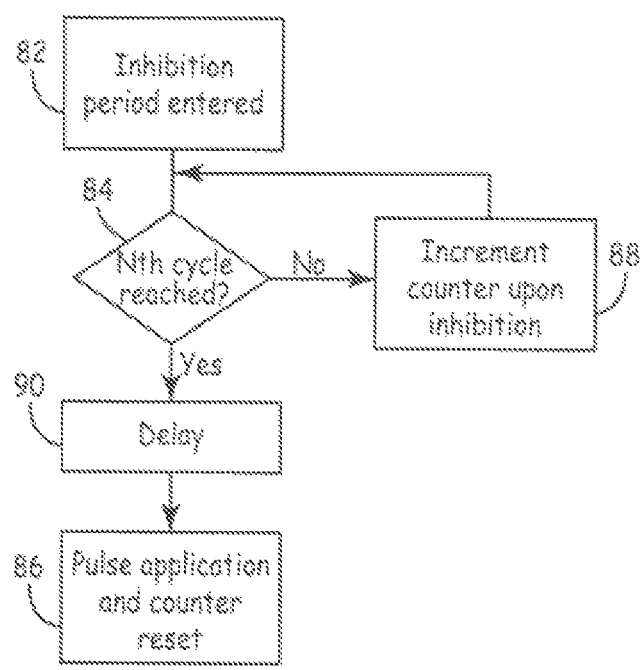
FIG. 7 is a flow chart illustrating another mode of operation of an implantable medical device operating according to the invention.

Another alternative embodiment is depicted in the flow chart illustrated in FIG. 7. FIG. 7 is like FIG. 6 except that FIG. 7 includes a delay 90 prior to pulse 86. When the heart receives a pacing stimulus that evokes depolarization, the cardiac tissue enters a brief refractory period, during which the cardiac tissue is unable to respond to further stimulus. Following detection of the Nth cycle, delay 90 after a naturally-occurring stimulus permits the cardiac tissue to enter the refractory period, during which pulse 86 is applied to compensate for drift. Pulse 86 is not effective in evoking a depolarization and does not affect the natural cardiac cycle because the cardiac tissue will not respond to pulse 86 during the refractory period. The delay needed to allow the cardiac tissue to enter a refractory period is normally short, about a tenth of a second.

Figure 8:
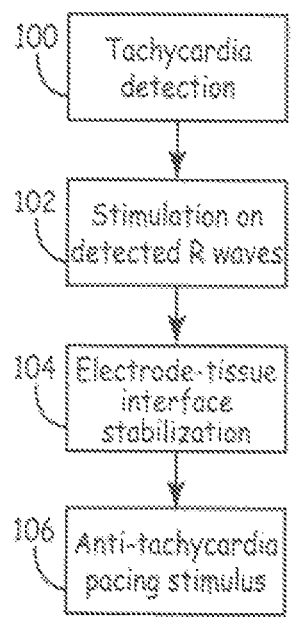
FIG. 8 is a flow chart illustrating another mode of operation of an implantable medical device operating according to the invention.

FIG. 8 is a flow chart depicting a further embodiment of the invention. Tachycardia, or rapid heart beat, may be a serious condition. Ventricular tachycardia or VT can be life-threatening. Stimulations used to treat tachycardia are more effective when the T-wave can be detected, but pace polarization artifacts prevent or hinder T-wave detection. When tachycardia is detected 100, such as by detection of a high frequency of R-waves, an IMD may apply one or more pulses 102. Pulses may be applied 102 quickly after R-wave detection and administered during a cardiac refractory period, during which the cardiac tissue is unable to respond to the stimuli. Applied pulses 102 counteract polarization signal drift, i.e., stabilize the polarization signal at the electrode-tissue interface 104. Following stabilization 106, T-wave detection is enhanced, and anti-tachycardia pacing stimulation may take place 106, using the T-wave as a benchmark. Pacing stimuli triggered by the falling edge of the T-wave may bring the tachycardia under control and restore normal sinus rhythm. Also, anti-tachycardia pacing therapies that are T-wave triggered can create extra stimuli that increase T-wave sensing reliability.

Figure 9:
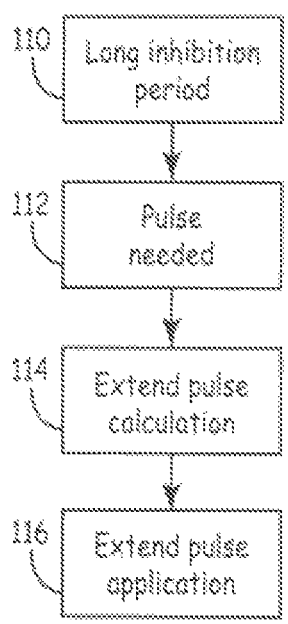
FIG. 9 is a flow chart illustrating another mode of operation of an implantable medical device operating according to the invention.

FIG. 9 is a flow chart depicting a further embodiment of the invention. In the embodiment illustrated in FIG. 9, a pulse applied after a long period of inhibition 110. When a pulse is needed 112 following a long inhibition period 110, the IMD calculates an amount by which the pulse should be extended 114 and applies an extended pulse 116. An extended pulse has a longer pulse width than an ordinary pulse. In some circumstances, the IMD may determine that multiple extended pulses are appropriate. The IMD may also adjust the wave shape of the pulse for enhanced efficiency. The extended pulse does not generate additional depolarizations of cardiac tissue but alters the storage of charge in the tissue, thus reducing the drift of the polarization signal and stabilizing the electrode-tissue interface.

In calculating the characteristics of the extended pulse 114, typically the amount of extension of pulse width depends upon the amount of drift. The amount of drift in turn depends upon the length of the inhibition period, upon the characteristics of the electrode and upon the characteristics of the patient's body. Microcomputer circuit 58 may include learning algorithms to use past results as a basis for calculating the length of the pulse extension for a particular patient with a particular inhibition period. The object of the learning is to determine, for a particular patient with a particular inhibition period, the characteristics of pulses that tend to stabilize the electrode-tissue interface. Past results may indicate whether a pulse of a longer or shorter duration is indicated for a particular inhibition period for a particular patient. The learning algorithms may also calculate whether more than one extended pulse may be beneficial, or whether a particular wave shape is beneficial. After a brief trial-and-error learning phase, microcomputer circuit 58 may calculate the characteristics of an appropriate extended pulse 114 in an efficient manner. An advantage of this method is that it may use fewer pulses to stabilize the electrode-tissue interface than other methods.

The preceding specific embodiments are illustrative of the practice of the invention. It is to be understood, therefore, that other expedients known to those skilled in the art or disclosed herein, may be employed without departing from the invention or scope of the appended claims. The present invention is also not limited to pacemakers per se, but may find further application for other medical devices that electrically interface with the heart. The present invention further includes within its scope methods of making and using the implantable medical device described above.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of wooden parts a nail and a screw are equivalent structures.

This application is intended to cover any adaptation or variation of the present invention. It is intended that this invention be limited only by the claims and equivalents thereof.

The invention claimed is:

1. A method for countering pacemaker post pace polarization artifact, comprising:
   sensing intrinsic electrical activity of the heart;
   waiting for a plurality of unpaced consecutive cycles having intrinsic activity to stabilize a lead and tissue interface; and
   delivering a polarization stabilization stimulation responsive to the occurrence of the plurality of unpaced consecutive cycles, the stimulation being coordinated with the sensed intrinsic activity.

2. The method of claim 1, wherein the polarization stabilization stimulation is delivered following a sensed R-wave.

3. The method of claim 1, wherein the polarization stimulation is delivered during a refractory period following a sensed R-wave.

4. A method for countering pacemaker post pace polarization artifact, comprising:
   sensing intrinsic electrical activity of the heart;
   waiting for an occurrence of a defined number of unpaced consecutive cycles having intrinsic activity to stabilize a lead and tissue interface; and
   delivering a polarization stabilization stimulation responsive to the occurrence of the defined number of unpaced consecutive cycles, the stimulation being coordinated with the sensed intrinsic activity.

5. The method of claim 4, wherein the polarization stabilization stimulation is delivered following a sensed R-wave.

6. The method of claim 4, wherein the polarization stabilization stimulation is delivered during a refractory period following a sensed R-wave.

7. A method for countering pacemaker post pace polarization artifact, comprising:
   sensing intrinsic electrical activity of the heart;
   waiting for a predetermined period of pacemaker inhibition extending over multiple cardiac cycles due to intrinsic cardiac activity; and
   delivering a polarization stabilization stimulation responsive to the occurrence of the predetermined period of pacemaker inhibition.

8. A method according to claim 7 wherein waiting for the predetermined period comprises waiting for an occurrence of a sequence of unpaced consecutive cycles having intrinsic activity to stabilize a lead and tissue interface.

9. The method of claim 7, wherein the polarization stabilization stimulation is delivered following a sensed R-wave.

10. The method of claim 7, wherein the polarization stabilization stimulation is delivered during a refractory period following a sensed R-wave.

* * * * *

UNITED STATES PATENT AND TRADEMARK OFFICE
CERTIFICATE OF CORRECTION

| | |
|---|---|
| PATENT NO. | : 8,761,881 B2 |
| APPLICATION NO. | : 11/459469 |
| DATED | : June 24, 2014 |
| INVENTOR(S) | : Benardus F. M. Vonk et al. |

Page 1 of 1

It is certified that error appears in the above-identified patent and that said Letters Patent is hereby corrected as shown below:

In the Claims

Claim 1, Col. 14, line 9-10, delete "for a plurality of unpaced consecutive cycles" and insert in place thereof -- for a plurality of consecutive cycles --;

Claim 1, Col. 14, line 13-14, delete "plurality of unpaced consective cycles" and insert in place thereof -- plurality of consective cycles --;

Claim 7, Col. 14, line 42-43, delete "of pacemaker inhibition" and insert in place thereof -- of pacemaker inhibition of pacing pulse delivery --.

Signed and Sealed this
Tenth Day of February, 2015

Michelle K. Lee
*Deputy Director of the United States Patent and Trademark Office*